United States Patent [19]

Watanabe

[11] 4,196,736
[45] Apr. 8, 1980

[54] APPARATUS FOR CRUSHING A CALCULUS

[76] Inventor: Hiroki Watanabe, Hiei-daira, 3-37-3, Otsu, Japan, 520

[21] Appl. No.: 813,004

[22] Filed: Jul. 5, 1977

[30] Foreign Application Priority Data

Jul. 9, 1976 [JP] Japan ................................. 51/81579

[51] Int. Cl.² .............................................. A61B 17/00
[52] U.S. Cl. ....................................... 128/328; 128/7
[58] Field of Search ................... 128/328, 319, 303, 6, 128/7; 89/1 B; 102/30

[56] References Cited

U.S. PATENT DOCUMENTS

| 3,118,508 | 1/1964 | Friedman et al. | 102/24 HC |
| 3,125,108 | 3/1964 | Murphy | 89/1 B |
| 3,413,976 | 12/1968 | Roze | 128/328 |

FOREIGN PATENT DOCUMENTS 1105783  4/1961  Fed. Rep. of Germany ............. 102/22
1259503  1/1968  Fed. Rep. of Germany ........... 128/328

Primary Examiner—Robert W. Michell
Assistant Examiner—Michael H. Thaler
Attorney, Agent, or Firm—George B. Oujevolk

[57] ABSTRACT

An instrument to remove stones from the human body such as stones in the gall bladder or kidney. An intracavitary tube is inserted in the organ where calculus is produced having an explosive charging chamber at the tip thereof. This explosive charging chamber is formed by a lid made of rigid material like metal except a fragile part made of less rigid materials and a triggering device for igniting the explosive from outside. The intracavitary tube is inserted into the organ, and the explosive charging chamber is brought near or in contact with the calculus, and then exploded to inflict a destructive force upon the calculus to crush it into small pieces, and the crushed small pieces are then eliminated from the human body.

3 Claims, 6 Drawing Figures

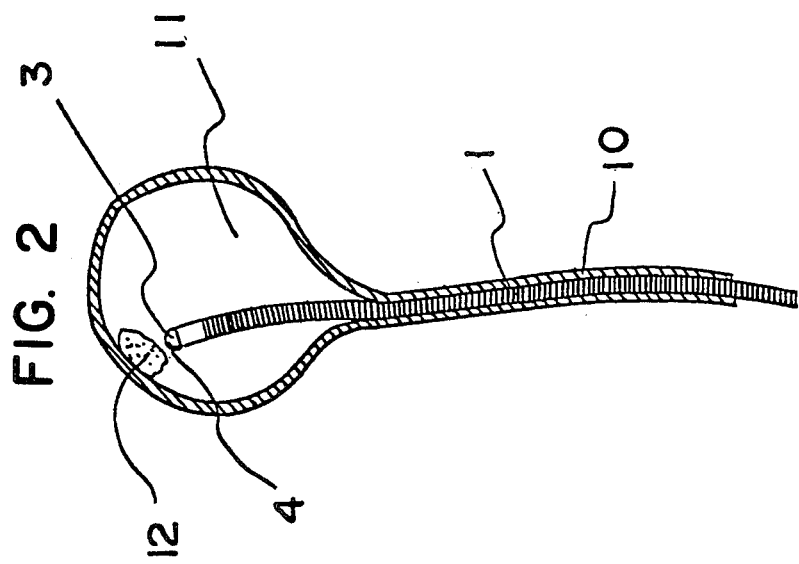
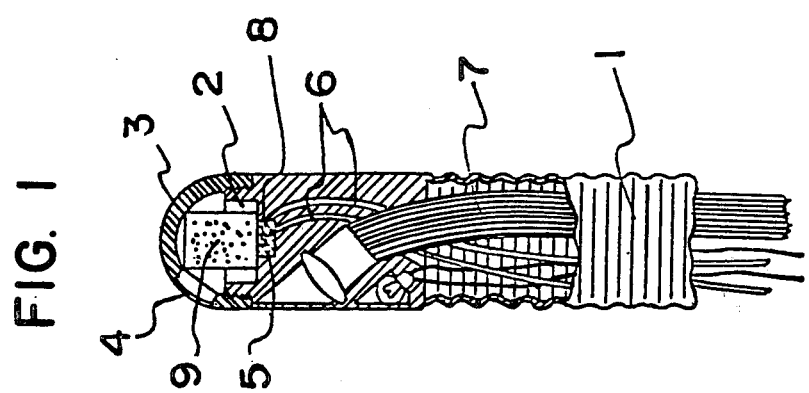

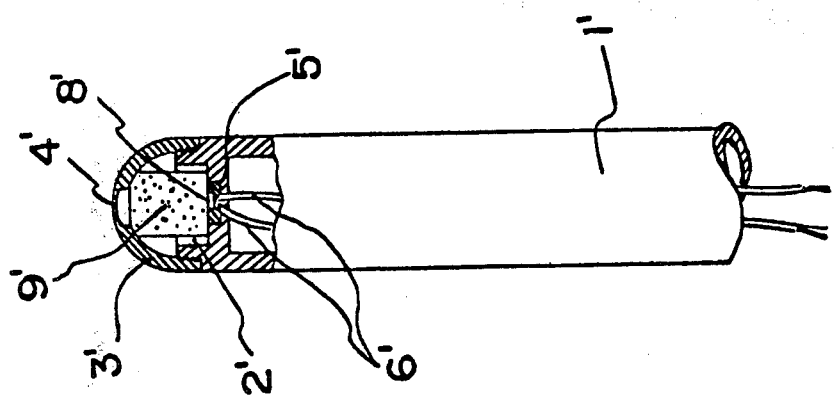
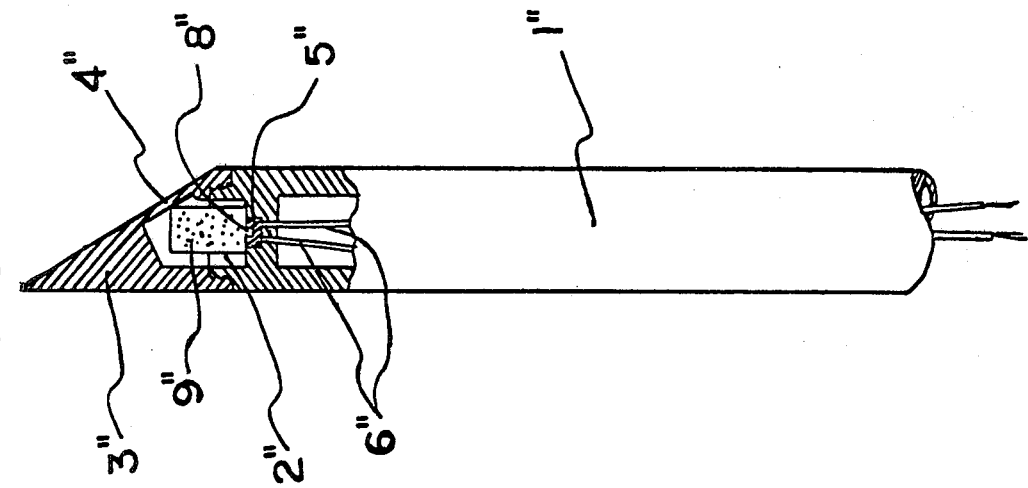

APPARATUS FOR CRUSHING A CALCULUS

BACKGROUND OF THE INVENTION

The present invention relates to a medical instrument for the removal of stones such as gall and kidney stones from the human body and to a method and apparatus for crushing a calculus, more particularly to a method and apparatus for crushing a calculus into small pieces without damaging the organ at all by means of large destructive force due to the explosion.

BRIEF DESCRIPTION OF THE PRIOR ART

Heretofore, such lithotrity for human organs have included:

(a) a method consisting of grasping the calculus and squashing it into small pieces by means of special lithotrity tools, blindly or observing with an endoscope;

(b) a method wherein an ultrasonic oscillator is inserted up to a position near the calculus in order to radiate ultrasound thereon and destroy it;

(c) a method wherein an electric spark is generated near the calculus to destroy it with shock waves.

However, it is hard to crush a calculus produced in an organ by the methods mentioned though they are useful in case of lithotrity in urinary bladder. It is difficult to produce a destructive force sufficient to crush a calculus produced in any organ except the urinary bladder by the methods (b) and (c) mentioned above.

OBJECTS OF THE INVENTION

Accordingly, it is a general object of the present invention to provide a method and apparatus for crushing a calculus which is useful not only in case of lithotrity in the urinary bladder but also in case of lithotrity in any organ such as organs in urinary tract other than the urinary bladder or organs in bile tract.

It is another object of the present invention to provide a method and apparatus for crushing a calculus which gives a large destructive force to crush a calculus.

It is another object of the present invention to provide a method and apparatus for crushing a calculus by which the crushed small pieces of the calculus are not dispersed in the organ.

It is further an object of the present invention to provide an apparatus for crushing a calculus having a reasonable small size, which is very light in weight and is mechanically simple.

SUMMARY OF THE INVENTION

Generally speaking the present invention contemplates a method for crushing a calculus relating to use of an explosive capable of obtaining large destructive force, its explosive are charged in the explosive charging chamber and is brought near or in contact with the calculus, and then the explosive is exploded in order to crush the calculus into small pieces in such a way as inflicting the destructive force due to the explosion concentratedly onto the calculus only. It is preferable to place some viscous material round the calculus before the explosion. The apparatus for carrying out the method relating to the present invention comprises an intracavitary tube capable of being inserted into an organ wherein the calculus may be produced, which is provided with the explosive charging chamber at the tip thereof, and the explosive charging chamber is formed by a lid made of some rigid material like metal and a triggering means for igniting the explosive from outside. A part of lid is made thinner than other parts in wall thickness or a fragile part made of less rigid material is formed thereon, which will be destroyed by force of the explosion energy.

As a lithotrity in any organ, the method and apparatus for crushing the calculus of this invention can inflict large destructive force concentratedly upon a calculus and will crush not only the calculus produced in the urinary bladder but also the calculus produced in any organ such as organs in urinary tract other than the urinary bladder or organs in bile tract into small pieces with effect.

Besides, in the method and apparatus for crushing the calculus of this invention, the wall of the organ will not be damaged because the destructive force to crush the calculus is concentrated upon the calculus only and the calculus is covered by viscous material so as not to disperse the crushed small pieces.

Other features, advantages and additional objects of this invention will appear more fully from the following description of embodiments with reference to the accompanying drawings in which:

BRIEF DESCRIPTION OF THE DRAWINGS

FIG. 1 is a side elevational view, partly broken away to show interior construction, of a preferred embodiment of this invention, FIG. 2 is an explanatory view of a condition of use a preferred embodiment shown in FIG. 1, FIGS. 3, 4 and 5 are side elevational views, partly broken away to show interior construction, of another embodiments of this invention.

DESCRIPTION OF THE PREFERRED EMBODIMENT

Figure 5:
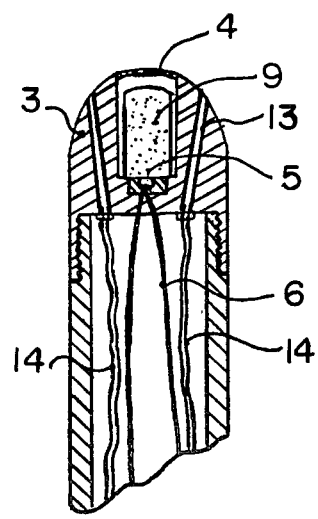

Explaining an embodiment of said lithotrity device for the urinary bladder referring to FIG. 1, a chamber (2) made of some rigid material like metal is formed at the tip of a flexible tube (1), on the tip thereon a lid (3) capable of keeping the inside airtight and watertight is provided.

A part of said lid (3) is made thinner than its other parts in wall thickness or a fragile part (4) made of less rigid material is attached thereon.

An electrically triggering means (5) is housed in said chamber (2) and a lead wire (6) connected thereto is led out up to the hand of operator through said flexible tube (1).

Said flexible tube (1) is utilized with an endoscope (7) in such a way that the surroundings of the tip part thereof can be observed thereby.

Next, explaining an embodiment of procedure by said device in case of the urinary bladder calculus referring to FIG. 2, said lid (3) is removed from said chamber (2), a triggering agent (8) is charged into said triggering means (5), and a kind of explosive (9) is charged into said chamber (2).

After that, said flexible tube (1) is inserted through the urethra (10), the tip thereof is made reached up to the inside of the urinary bladder (11), and said fragile part (4) of said chamber (2) at the tip of said flexible tube (1) is made faced to the calculus (12), observing said calculus (12) by means of said endoscope (7).

Then energizing said triggering means (5) through said lead wire (6) will explode said triggering agent (8), resulting in inducing the explosion of said explosive (9) thereby.

Said fragile part (4) will be destroyed by force of the explosion energy brought about at the time, and the destructive energy will hit directly the front side of said fragile part (4), that is, the calculus (12) positioned facing to the tip face of said flexible tube (1), resulting in smashing of the calculus (12) into small pieces.

After completing the sequence of processes mentioned, said flexible tube (1) is to be pulled out and then the smashed small pieces of calculus are to be removed from the urinary bladder by water spray.

Lid (3) may be provided on the side of said chamber (2) without being provided on the tip thereof; in this case, the destructive energy of explosive will be directed to the side of said chamber (2).

As for the kind of explosive used in this invention, lead azide or silver azide is most suitable because they are sure to be triggered to explode easily even with a very small amount thereof. Although as to the kind of triggering agent, generally used ignitor or detonator may be used, the triggering agent can be omitted when some sensitive explosive such as said lead azide or silver azide are employed as for said explosives.

As for the kind of triggering means, an electric means is used; wherein it can be energized to actuate by means of a lead wire passed through said intracavitary tube; however, other kind of triggering means may be adopted, too, if suitable.

It is also possible that an intracavitary tube is not utilized in combination with an endoscope but utilized in parallel with another endoscope so as to be brought near or in contact with a calculus with respect to the tip thereof.

FIG. 3 shows an intracavitary tube having no endoscope therein, wherein a chamber (2') made of rigid material like metal is formed at the tip of an urethra tube (1') and besides a lid (3') capable of keeping the inside airtight and watertight is provided at the tip thereof.

A fragile part (4') is provided at the tip of said intracavitary tube in such a way that a part of said lid (3') is formed to be thinner than the other part thereof or a material of less rigidity is attached thereon.

An electric triggering means (5') is housed in said chamber (2') wherein a lead wire (6') connected thereto is led out to the hand of operator through said urethra tube (1').

As for the method for crushing the urinary bladder calculus by means of the device mentioned above, a triggering agent (8') and explosive (9') are charged in said chamber (2') and said device is inserted into the urinary bladder through the urethra until said fragile part (4') is approached to be faced with a calculus, observing the position of the calculus in the urinary bladder by means of roentgenograhy or watching directly the position of the calculus in such a way as inserting a cystoscope through the urethra, and then said explosive (9') are made explode in order to smash the calculus into small pieces.

FIG. 4 shows another kind of lithotrity device capable of smashing a calculus produced in any organ of human body by the puncture of body wall, wherein a chamber (2") made of rigid material like metal is formed at the tip of a rigid tube (1"), and a lid (3") capable of keeping the inside airtight and watertight is provided at the tip thereof, and the tip is to be made sharp-angled.

A part of said lid (3") is formed to be thinner than the other part thereof or a material of less rigidity is to be attached thereto to provide a fragile part (4").

An electric triggering means (5") is housed in said chamber (2") and a lead wire (6") connected thereto is to be lead out to the hand of operator through said rigid tube (1").

As for the method for crushing the urinary bladder calculus by means of the device mentioned above, a triggering agent (8") and explosive (9") are charged in said chamber (2") and abdominal wall is punctured until the tip thereof is approached to be faced with a calculus in the urinary bladder, observing the position of the calculus in the urinary bladder by means of roentgenography or watching directly the position of the calculus in such a way as inserting a cystoscope through the urethra, and then said explosive (9") are made explode in order to smash the calculus into small pieces.

The experimental example of this invention are as follows;

Table 1, show the result of the test performed of crushing some calculus outside the body by means of the lithotrity device; wherein a calculus of 2.4 mm to 12 mm in minimum diameter, which has been taken out of the body, is to be attached to the tip of an intracavitary tube made of stainless steel of 1.5 mm in inner diameter with a piece of adhesive tape and then an explosive of lead azide or silver azide of 0.5 mg to 16 mg in weight has been made explode.

Table 1

| Sample | Minimum diameter of calculus (mm) | Explosive (lead azide or silver azide) | | Result* |
|---|---|---|---|---|
| | | Density (g/cm$^3$) | Weight (mg) | |
| 1 | 2.4 | 2.04 | 2.8 | O |
| 2 | 3.6 | 2.11 | 0.6 | X |
| 3 | 3.6 | 2.11 | 0.6 | Δ |
| 4 | 3.8 | 2.04 | 1.7 | O |
| 5 | 3.8 | 2.03 | 1.0 | O |
| 6 | 4.0 | 2.11 | 0.7 | X |
| 7 | 5.3 | 2.92 | 3.4 | O |
| 8 | 7.5 | 2.03 | 1.8 | X |
| 9 | 7.5 | 3.38 | 5.2 | Δ |
| 10 | 9.0 | 3.50 | 6.8 | O |
| 11 | 10.0 | 2.00 | 16.5 | O |
| 12 | 12.0 | 4.00 | 5.7 | O |

*O smashed
X crushed into a few pieces
Δ no change

From the result shown above, it has proved that such an ordinary-size calculus as having the minimum diameter of approx. 3.8 mm can be crushed effectively with a piece of explosive of lead azide or silver azide of approx. 1 mg in weight, and that the quantity of explosive necessary to crush calculus depending on the size of calculus generally.

Next, Table 2 shows the result of the test observed of the damaged condition of the opened rabbit bladder wall, the intracavitary tube containing the explosive shown in above mentioned enbodiment has been approached directly to the bladder wall with a definit distance therebetween being changed to be several cases; after the explosion, the damaged condition of the bladder wall has been examined histologically.

Table 2

| Case No. | Distance from Mucosa surface (cm) | Explosive (Silver azide) Density (g/cm$^3$) | Weight (mg) | Histrogical finding on bladder wall | | | | |
|---|---|---|---|---|---|---|---|---|
| | | | | Mucosa | Submucosa | Musculosa | Serosa | Perforation |
| 1 | 2.0 | 3.34 | 6.1 | + | + | + | — | — |
| 2 | 1.5 | 3.54 | 4.8 | ± | ± | — | — | — |
| 3 | 1.0 | 3.51 | 4.2 | ± | — | — | — | — |
| 4 | 0.5 | 2.46 | 2.0 | + | + | — | — | — |
| 5 | 0 | 2.46 | 2.9 | ++ | ++ | + | — | — |

—: No change
±: Slight bleeding
+: Narrowing of layer
++: Destructed

As seen from the test result shown above, it has proved that not only it can be avoided perfectly to allow the inner wall of organs to be damaged such as perforated, but also the mucous membrane can be prevented of its being so damaged as to be troubled even if it may be narrowed in its thickness only by selecting the amount of explosive to be reduced to some degree and besides by taking the distance between the explosive and the inner wall of organ to be larger.

Next, reporting the result of our other experiment, in this experiment we used 5 mg of silver azide molded to be cylindrical with a mold as said explosive (9) in FIG. 1; the process was such that said explosive is charged in a chamber (1), a calculus of approx. 10 mm in diameter taken out of the urinary bladder of human body was housed in the incised urinary bladder of an adult dog, said fragile part (4) was brought near or in contact with the calculus, and then the wall of the urinary bladder was closed by suture; after that, the triggering means was energized to explode the explosive (9). Exploring the result of the experiment by reincising the urinary bladder again immediately after the explosion, it was found that the calculus was successfully smashed into small pieces due to the destructive energy of the explosion concentrated thereon by the destruction of said fragile part (4); besides, no miscropic abnormality was found on the inside wall of the urinary bladder, and also no abnormality was found on the same part of the urinary bladder on the second exploration performed by re-incising the urinary bladder several weeks after the first experiment.

Further in order to reduce the damage of mucous membrane, we have further carried out such an experiment as follows:

As it has often been seen such a case that the mucous membrane near the explosive is damaged with the scattered broken pieces of calculus crushed by dint of the explosion occurred, I have tried such an experiment to provide a buffer means that the calculus and the mucous membrane near thereto are to be covered with some mucous membrane just before the explosion in such a way as injecting some viscous material such as jelly, etc. thereinto.

Figure 6:
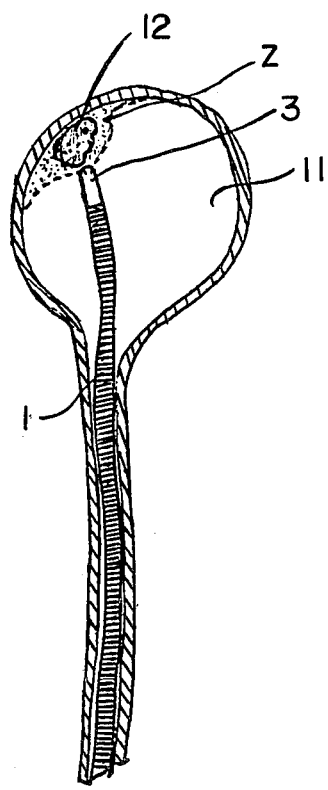
FIG. 6 is an explanatory view of a condition of use a preferred embodiment shown in FIG. 5.

FIG. 5 shows the embodiment to make the experment mentioned above in the explosion of a calculus in the urinary bladder, and FIG. 6 shows an embodiment of said intracavitary tube (1) equipped with said jelly jetting nozzle (13).

The procedure of the experiment mentioned above to crush a calculus is as follows:

Insert said intracavitary tube (1) into an organ of the human body, feed some viscous material into the organ from outside through said feed pipe (14) connected to said nozzle (13) with the tip of said intracavitary tube (1) inserted is slightly in contact with said calculus (12), cover the around of calculus and surface of mucous membrane near thereto with said jelly material (Z) in such a way as jetting out it out of said nozzle (13), and then make an explosion to crush said calculus by actuating the igniting means.

If this method mentioned above is adopted, the mucous membrane will not be damaged much in spite of using much explosive for the explosion; therefore, not only even large-size calculus can be crushed completely but also an effective explosion can be carried out even in such a case that the inner wall of an organ of the human body is closely adjacent to a calculus such as the explosion case of calculus in the urinary tube of the human body, etc.

It is recommended that said viscous material is harmless to the human body and can be eliminated easily out of the body with washing out etc. after the treatment, for example, "Lidocain jelly" is prefer.

I claim:

1. A medical instrument for crushing a calculus in a human body organ, comprising in combination:
    (a) an elongated flexible intracavitary tube (1) sized for insertion into a human body passage to a location in the human body wherein a calculus may be formed or in the process of production, said tube having defined forward and rear ends;
    (b) an explosive charging chamber (2) for holding an explosive charge, of rigid material defined at said forward end;
    (c) an airtight and watertight removable lid (3) over said chamber at said forward end, said lid (3) having a destructible thin outer portion (4);
    (d) electrical trigger means (5) housed in said chamber for detonating an explosive charge placed in said chamber, with a lead wire (6) leading out of said rear end; and,
    (e) elongated endoscope means with an outer viewing section at said forward end held by said tube, and a fiberglass tube means coupled to said viewing section extending out of the rear end.

2. The apparatus for crushing a calculus as defined in claim 1, comprising jet nozzle means of gel-state material provided at the forward end of said intracavitary tube, feed pipe means connected to said jet nozzle for feeding said gel-state material, and said feed pipe means housed in said intracavitary tube.

3. The apparatus for crushing a calculus as defined in claim 1, and its forward end formed into a puncture needle.

* * * * *